United States Patent
Wu et al.

(10) Patent No.: US 9,950,192 B2
(45) Date of Patent: Apr. 24, 2018

(54) METHOD FOR FIDUCIALLESS REAL-TIME TRACKING IN RADIATION TREATMENT OF ABDOMINAL TUMORS

(71) Applicants: Xiaodong Wu, North Miami, FL (US); George F Hatoum, Miami, FL (US)

(72) Inventors: Xiaodong Wu, North Miami, FL (US); George F Hatoum, Miami, FL (US)

( * ) Notice: Subject to any disclaimer, the term of this patent is extended or adjusted under 35 U.S.C. 154(b) by 50 days.

(21) Appl. No.: 14/998,039

(22) Filed: Apr. 22, 2014

(65) Prior Publication Data
US 2017/0209713 A1    Jul. 27, 2017

(51) Int. Cl.
*A61N 5/00*    (2006.01)
*A61N 5/10*    (2006.01)

(52) U.S. Cl.
CPC ......... *A61N 5/1037* (2013.01); *A61N 5/1049* (2013.01); *A61N 5/1067* (2013.01); *A61N 2005/1061* (2013.01)

(58) Field of Classification Search
CPC .... A61N 5/1049; A61N 5/1064; A61N 5/107; A61N 2005/1062; A61N 5/103; A61N 5/1037
USPC ............... 600/1-2; 250/491.1, 492.1, 492.3; 378/62-65, 68-69
See application file for complete search history.

(56) References Cited

U.S. PATENT DOCUMENTS

| 8,042,209 B2 * | 10/2011 | D'Souza | A61N 5/1049 5/610 |
| 2012/0292534 A1 * | 11/2012 | Geneser | A61N 5/1069 250/492.3 |
| 2014/0107390 A1 * | 4/2014 | Brown | A61N 5/1045 600/1 |

* cited by examiner

*Primary Examiner* — John Lacyk
(74) *Attorney, Agent, or Firm* — Calrie Marsh, Esq.; Calrie Marsh, P.A.

(57) ABSTRACT

A method for fiducial-less real-time motion tracking of abdominal tumors based on the correlation between the patient's breathing pattern and the diaphragm/lung border during treatment delivery. This invention utilizes an edge detection technique to delineate the diaphragm/lung border on radiographic images in order to calculate or determine tumor locations in the abdomen. The position of the diaphragm/lung border is synchronized with the breathing pattern obtained from continuous optical monitoring of a patient's respiratory cycle. The real-time optical breathing pattern obtained from monitoring is used to determine or calculate the position of the diaphragm/lung border during treatment delivery. The position of the diaphragm/lung border is then used to determine the tumor location in real-time. The target tumor coordinates generated through this process are used by the treatment delivery system to adjust the radiation beam geometry of the treatment delivery system to follow the tumor in real-time and accurately deliver radiation dose.

2 Claims, 3 Drawing Sheets

METHOD FOR FIDUCIALLESS REAL-TIME TRACKING IN RADIATION TREATMENT OF ABDOMINAL TUMORS

CROSS-REFERENCE TO RELATED APPLICATIONS

This application claims the benefit of U.S. Provisional Application No. 61/814,772 filed on Apr. 22, 2013. The entire disclosure of this prior application is hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

The present invention relates generally to external beam radiation treatment of abdominal tumors with increased accuracy in light of normal organ and respiratory motion during treatment delivery.

BACKGROUND OF THE INVENTION

Radiation therapy has been one of the three effective treatment modalities in cancer management. it has been a current technical endeavor to further improve radiation treatment efficacy by increasing targeting accuracy, i.e. the delivery of radiation doses directly to the target tumor while limiting the damage/radiation exposure to surrounding healthy tissue. One of the major challenges in this endeavor is the movement or motion of a tumor due to normal respiration during radiation treatment delivery. There have been a number of technologies developed to overcome this challenge. They are notably: respiratory gating; breath holding; and real-time tumor tracking. Of these three techniques, the real-time tumor tracking is considered the most optimal. There are few techniques used for real-time tumor tracking. The most frequently used techniques for real-time tumor tracking involve the use of radio-opaque tumor surrogates (fiducials) such as metallic seeds (e.g. Synchrony Respiratory Tracking System by Accuray, Inc) or radio-frequency transponders (e.g. Calypso® System), which require invasive procedures to implant the surrogates inside or around tumors.

On the other hand, non-invasive techniques for real-time tumor tracking has been actively sought after for treatment of sensitive areas such as the lung, which has historically been challenging. Fiducial-less real-time tracking techniques have been developed and clinically implemented for lung tumors located in selective regions in which radiographical visualization is possible (e.g. Xsight Lung, Accuray, Inc). Fiducial-less real-time motion tracking for abdominal tumors, such as liver tumors and pancreatic tumors, however remains a challenge, where no commercial, practical solution is currently available for clinical use. One of the main contributing factors to the difficulties of fiducial-less motion tracking of abdominal tumors is the inability to visualize abdominal tumors in non-volumetric types of radiographic images. Much like the advent of fiducial-less motion tracking for lung tumors, the present invention describes a new approach for fiducial-less real-time tracking of abdominal tumors.

SUMMARY OF THE INVENTION

The present invention provides a method for overcoming the challenges relating to fiducial-less real-time motion tracking of abdominal tumors, such as liver tumors and pancreatic tumors. The aim of this invention is to provide clinicians with a method for determining the location of abdominal tumors in non-volumetric types of radiographic images. This invention utilizes the diaphragm/lung border on radiographic images to calculate or determine tumor locations in the abdomen. The position of the diaphragm/lung border is synchronized with the breathing pattern obtained from continuous optical monitoring of a patient's respiratory cycle. The real-time optical breathing pattern obtained from monitoring is used to determine or calculate the position of the diaphragm/lung border during treatment delivery. The position of the diaphragm/lung border is then used to determine the tumor location in real-time. The target tumor coordinates generated through this process are used by the treatment delivery system to adjust the radiation beam geometry to follow the tumor in real-time. The present invention aims to increase the accuracy of radiation delivery to abdominal tumors by utilizing fiducial-less real-time tracking of organ motion to predict the precise location of abdominal tumors.

BRIEF DESCRIPTION OF THE DRAWING(S)

In describing the invention, reference will at times be made to the accompanying drawings in which.

DESCRIPTION OF THE INVENTION

Before the subject invention is described further, it is to be understood that the invention is not limited to the particular embodiments of the invention described below, as variations of the particular embodiments may be made and still fall within the scope of the invention. It is also to be understood that the terminology employed is for the purpose of describing particular embodiments, and is not intended to be limiting.

The details of one or more embodiments of the invention are set forth in the accompanying drawings and the description below. Other features, objects, and advantages of the invention will be apparent from the description and drawings, and front the claims. In the following description, numerous specific details are set forth to provide a thorough understanding of the embodiments. One skilled in the art to which this invention belongs will recognize, however, that the techniques described can be practiced without one or more of the specific details, or with other methods, components, materials, etc. In other instances, well known structures, materials or operations are not shown or described in detail to avoid obscuring certain aspects.

In this specification, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Figure 1A:
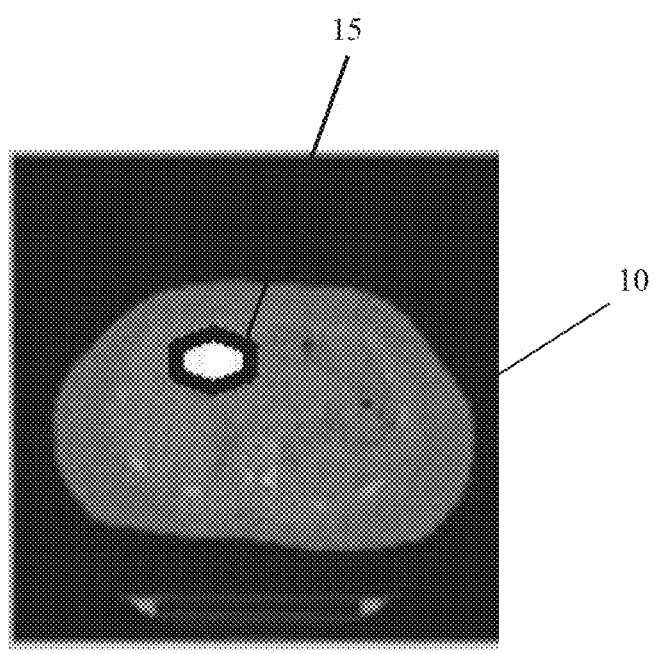
FIG. 1A is a CT image of a liver tumor.
Figure 1B:
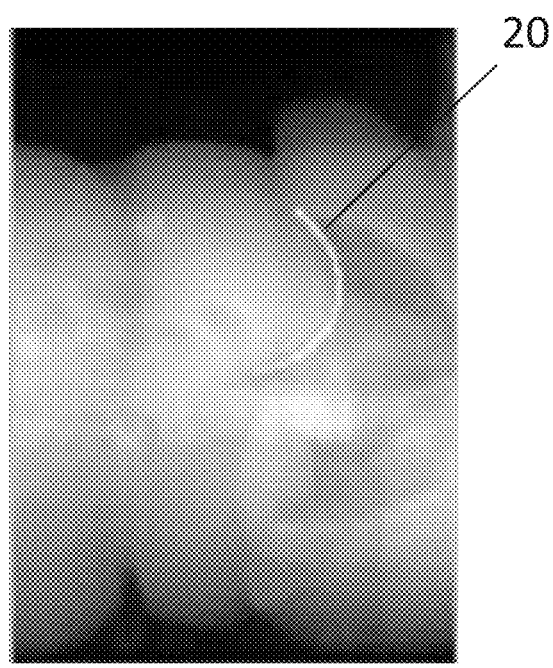
FIG. 1B is a 45-degree oblique Digital Reconstructed Radiograph (DRR) with the diaphragm/lung border delineated.
Figure 1C:
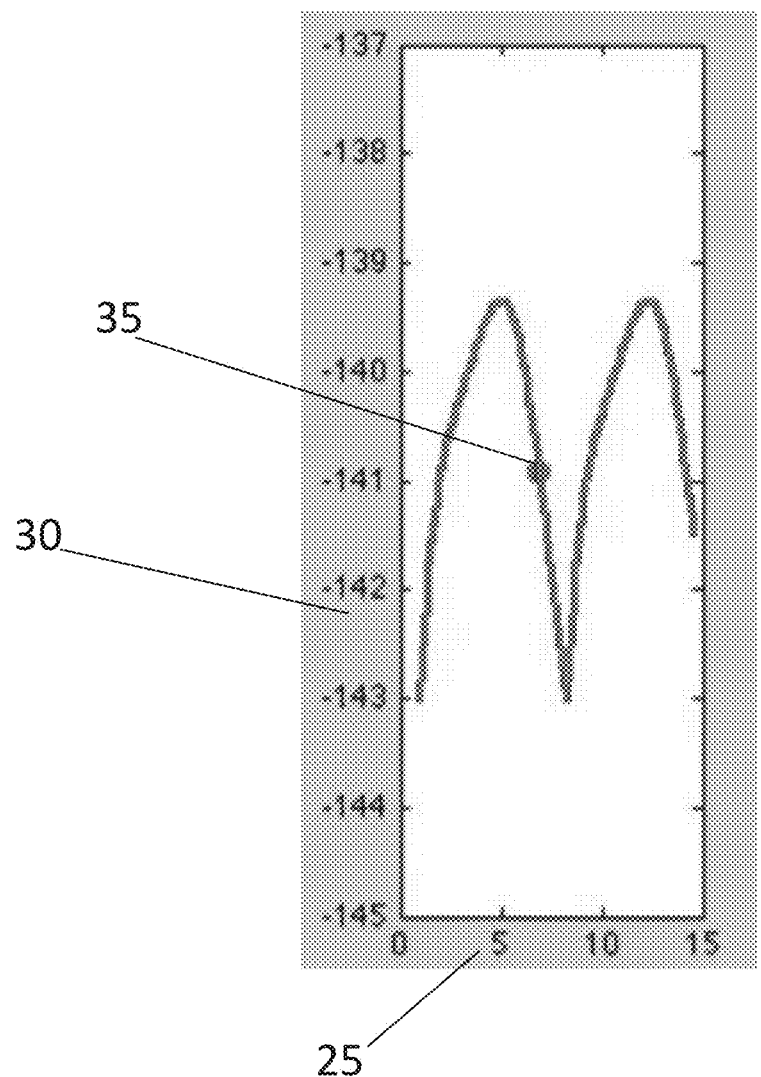
FIG. 1C is a graph of the breathing curve during treatment.

FIG. 1A is a CT image of a liver 10 showing a tumor 15 (contoured), FIG. 1B is a 45-degree oblique Digital Reconstructed Radiograph (DRR) of the abdominal area wherein the diaphragm/lung border 20 is delineated. FIG. 1C is a graph of the breathing curve during treatment where the x-axis 25 shows time and the y-axis 30 shows amplitude.

The essence of the invention is to use the diaphragm/lung border 20 dileanated on radiographic images to determine or calculate tumor locations in the abdomen. The position of the diaphragm/lung border 20 is synchronized with the breathing pattern obtained from continuous optical monitoring of the patient's respiratory cycle. During treatment delivery, the real-time optical breathing pattern is used to determine or calculate the position of the diaphragm/lung border 20, and the position of the diaphragm/lung border 20 is in turn used to determine the tumor location(s) in real-time. The tumor coordinates generated from these calculations are then used by the radiation treatment delivery system to adjust the radiation beam geometry to follow the tumor in real-time.

In the preferred embodiment of the invention, a patient will first undergo 4D-CT acquisition where multiple-phase (minimum of eight phases is preferred) CT image sets are reconstructed. 4D CT scans are used to reduce motion artifacts or distortions to tumor image, which can result from respiratory organ motion with the use of free breathing 3D scanning. The 4D CT image sets are imported into the radiation treatment planning system for treatment planning. The tumor volume is delineated on each phase-CT. The radiation treatment plan is developed using a CT set of a certain breathing phase. A reference alignment point is chosen in a stationary skeletal region of the patient's chest area. The radiation beam geometries are configured in relation to this anatomically stationary alignment point. Stereotactic DRR pairs are then generated for each phase-CT as shown in FIG. 1B. On each DRR, edge detection technique is used to delineate the diaphragm/lung border 20. At this juncture, each DRR pair of diaphragm/lung border 20 is associated with one specific tumor location and shape obtained from the CT images of corresponding phase, and a mathematical correlation is established such that at any arbitral point of the respiratory cycle the diaphragm/lung border 20 of a DRR (pair) can be used to determine the abdominal tumor location and shape.

During treatment delivery, the patient will he setup based on the pre-specified stationary alignment point. Thus, the anatomic alignment point will be positioned at the origin or central axis of the radiation delivery system. This is achieved by radiographically aligning the skeletal structure, which position is minimally influenced by respiratory motion. Following this initial setup, monitoring of breathing pattern is established using optical beacons affixed on the patient's chest wall and the stereotactic radiographic system is setup consistent with the DRR configuration. Stereotactic or single radiographic images are taken synchronized with the breathing pattern or curve, see FIG. 1C. The dot 35 on the breathing curve in FIG. 1C specifies the time at which radiographic images are taken.

After synchronizing the breathing pattern and the radiographic images, an edge detection technique is used to delineate diaphragm/lung border 20 on each radiographic image as shown in FIG. 1B. A correlation model is subsequently built such that one can determine the location of the diaphragm/lung border 20 solely from the breathing pattern (curve), as in FIG 1C. As the tumor location/shape has been correlated with the delineated diaphragm/lung border 20 through DRR's, one can determine or calculate tumor location in real-time by the breathing curve, during radiation treatment delivery. The real-time information of tumor location/shape can be used for feedback control, and radiation beam geometry (entry orientation and shape) can consequently be adjusted in real-time to follow the tumor for precise radiation dose delivery to the tumor.

This invention takes advantage of the fact that the diaphragm/lung border 20 can be accurately delineated from radiographic images, and therefore can be used as a surrogate to determine the location of abdominal tumors that move with respiratory motion. The development of this technique enables high precision real-time tracking of abdominal tumors without the risk and unnecessary complexity associated with the invasive implantation of fiducials, This new approach to fiducial-less real-time tumor tracking improves the treatment outcome with the reduction of toxicity generally associated with radiation therapy.

The accuracy of this technique has been verified using a computer simulation model to generate a virtual patient based on 4D CT scans. The simulation software used in testing this model successfully demonstrated an accurate correlation between diaphragm border and general location of an abdominal tumor.

It is be understood, that the subject invention described herein is not limited to the particular embodiments of the invention described herein, as variations of the particular embodiments may be made and still fall within the scope of the invention as described herein. It is also to be understood that the terminology employed is for the purpose of describing particular embodiments, and is not intended to be limiting.

As various changes can be made in the above-described subject matter without departing from the scope and the spirit of the invention is intended that all subject matter contained in the above description, shown in the accompanying drawings, or defined in the appended claims will be interpreted as descriptive and illustrative, and not in a limiting sense. Many modifications and variations of the present invention are possible in light of the above teachings. it is therefore to be understood that within the scope of the appended claims, the invention may be practiced otherwise than as specifically described.

EQUIVALENTS

Those skilled in the art will recognize, or be able to ascertain using no more than routine experimentation, many equivalents to the specific embodiments of the invention described herein. Such equivalents are intended to be encompassed by the claims.

What is claimed is:

1. A method for fiducial-less real-time motion tracking of abdominal tumors comprising:
   acquiring 4D CT scans of a patient's tumor and reconstructing multiple phase 4D CT image sets;
   importing the 4D CT image sets into a radiation treatment planning system for treatment planning which includes;
   delineating the tumor volume on each phase CT;
   utilizing a 4D CT image set corresponding to a specific breathing phase of the patient's respiratory cycle;
   choosing a reference alignment point in a stationary skeletal region of the patient for configuring the radiation beam geometry of the radiation treatment delivery system;
   generating stereotactic digital reconstructed radiograph pairs of each phase CT;

using an edge detection technique to delineate the diaphragm/lung border for each digital reconstructed radiograph whereby each pair of diaphragm/lung border corresponds to a tumor location and shape;

establishing a mathematical correlation between each pair of diaphragm/lung border and the tumor location, whereby at an arbitrary point of the respiratory cycle, the diaphragm/lung border of the digital reconstructed radiograph pair can be used to determine tumor location and shape;

delivering radiation treatment to the patient's tumor, comprising:

aligning the patient according to the pre-selected stationary skeletal alignment point, including positioning the alignment point at the central axis of the radiation delivery system;

monitoring the patient's breathing pattern utilizing optical beacons affixed to the patient's chest wall;

setting up a stereotactic radiographic system consistent with the previously generated digital reconstructed radiographs;

taking stereotactic or single radiographic images of the tumor volume and synchronizing the images with the breathing pattern obtained from optical monitoring of the patient's respiratory cycle;

utilizing an edge detection technique to delineate the diaphragm/lung border on each radiographic image;

generating a correlation model to calculate the location of the diaphragm/lung border from the breathing pattern established during treatment planning;

correlating the location and shape of the tumor with the calculated diaphragm/lung border through the digital reconstructed radiographs;

using the information from the correlation to predict or determine the location of the tumor during treatment in real-time;

tracking the tumor location and shape in real-time to deliver radiation treatment dose to the location of the tumor;

delivering radiation treatment to the tumor.

2. The method of claim 1 wherein the acquisition of 4D CT images requires a minimum of eight phases.

\* \* \* \* \*